(12) United States Patent
Enlow et al.

(10) Patent No.: US 6,747,167 B2
(45) Date of Patent: Jun. 8, 2004

(54) PROCESS FOR THE PREPARATION OF ACID ESTERS

(75) Inventors: William Palmer Enlow, Belpre, OH (US); Carloss La Verne Gray, Belpre, OH (US); Vaikunth Sitaram Prabhu, Morgantown, WV (US)

(73) Assignee: Crompton Corporation, Middlebury, CT (US)

( * ) Notice: Subject to any disclaimer, the term of this patent is extended or adjusted under 35 U.S.C. 154(b) by 0 days.

(21) Appl. No.: 10/253,080

(22) Filed: Sep. 23, 2002

(65) Prior Publication Data

US 2004/0059151 A1 Mar. 25, 2004

(51) Int. Cl.[7] ................................................. C07F 9/09
(52) U.S. Cl. ............................................. 558/90; 560/8
(58) Field of Search ................................. 558/90; 560/8

(56) References Cited

U.S. PATENT DOCUMENTS

| 5,618,866 A | 4/1997 | Prabhu et al. |
| 5,786,497 A | 7/1998 | Mahood et al. |

*Primary Examiner*—Deborah C. Lambkin
*Assistant Examiner*—Golam M M Shameem
(74) *Attorney, Agent, or Firm*—Michael P. Dilworth

(57) ABSTRACT

The present invention is directed to a process for the preparation of sterically hindered acid esters, e.g., organic phosphites, comprising contacting a sterically hindered hydroxyl-containing compound with an acid halide in the presence of an acid acceptor selected from the group consisting of: 1,5-diazabicyclo[4.3.0]non-5-ene (DBN), 1,8-diazabicyclo[5.4.0]undec-7-ene (DBU), 4-(dimethylamino)pyridine (DMAP), 1,4-diazabicyclo[2.2.2]octane (DABCO), or mixtures thereof, wherein said an acid acceptor is present in an amount sufficient to drive the reaction to completion.

15 Claims, No Drawings

PROCESS FOR THE PREPARATION OF ACID ESTERS

FIELD OF THE INVENTION

The present invention is directed to a process for the preparation of acid esters, including phosphoric add esters and carboxylic acid esters from sterically hindered phenols and alcohols.

BACKGROUND OF THE INVENTION

It is known to use acid acceptors to drive reactions wherein one of the reactants is sterically hindered, e.g., a sterically hindered phenol or alcohol. Typical reactions involving sterically hindered reactants include the preparation of esters from acid chlorides such as acyl halides, phosphorous or chlorophosphous compositions, e.g., the reaction between benzoyl chloride and 2, 4, 6, tri-t-butylphenol to make an ester such as 2, 4, 6, tri-t-butyl benzoate, or the reactions between the appropriate hydroxy compounds and phosphorous compounds, e.g., phosphorous trihalides, to prepare organic diphosphites.

For example, in the preparation of organic diphosphites, the ease of substitution of the halides decreases as the halide is replaced. In the preparation of neoalkyl aryl phosphites, the neoalkyl diol readily reacts in essentially quantitative conversion with a phosphorous trihalide to yield a di-substituted neoalkyl halo phosphite (i.e., an intermediate di-substituted phosphorohalidite). The displacement of the third halo group is less than quantitative and is considerably slower in rate. Additionally, displacement of the third halo group by a sterically hindered phenol is even more difficult and requires elevated temperatures and/or use of a catalyst.

In order to increase the rate of reaction and the degree of completion for displacing the third halide with a sterically hindered moiety, various techniques have been generally utilized in the art. These techniques include elevating the reaction mixture temperature and the use of a basic catalyst or a hydrogen halide acceptor, e.g., amines. U.S. Pat. No. 5,786,497 discloses the use of a polymeric amine to increase the rate of reaction in the production of organic phosphites to about 97%. U.S. Pat. No. 5618,866 generally discloses that 1,8-diazabicyclo[5.4.0]undec-7-ene (DBU) can be used in a reaction to produce organic phosphites.

There is still a need for an improved method to increase the conversion yields in reactions wherein one of the reactants is sterically hindered.

SUMMARY OF THE INVENTION

The invention relates to a two-stage process for the preparation of acid esters from acid halides and sterically hindered phenols and alcohols, with the second stage of the process being carried out after obtaining a conversion rate of at least about 95%, in the presence of an acid acceptor selected from the group consisting of: 1,5-diazabicyclo[4.3.0]non-5-ene (DBN), 1,8-diazabicyclo[5.4.0]undec-7-ene (DBU), 4-(dimethylamino)pyridine (DMAP), 1,4-diazabicyclo[2.2.2]octane (DABCO), or mixtures thereof, wherein the acid acceptor is present in an amount sufficient to drive the reaction to completion of at least 98%.

The invention also relates to the recovery of an acid acceptor selected from the group consisting of 1,5-diazabicyclo[4.3.0]non-5-ene (DBN), 1,8-diazabicyclo[5.4.0]undec-7-ene (DBU), 4-(dimethylamino)pyridine (DMAP) or 1,4-diazabicyclo[2.2.2]octane (DABCO), from a process for preparing acid esters from a reaction in which one of the reactants is a sterically hindered compound.

In one embodiment of the invention, the acid halides are phosphorous compounds for the preparation of phosphoric acid esters, e.g., organic phosphites.

In another embodiment of the invention, the acid halides are acyl halides, e.g., benzoyl chloride, benzoyl bromide, trichloroacetyl chloride, methyl benzoyl chloride, etc., for the preparation of carboxylic acid esters such as benzoates, toluates, etc.

DETAILED DESCRIPTION OF THE INVENTION

As used within, "sterically hindered" means a characteristic of molecular structure in which the molecules have a spatial arrangement of their atoms such that a given reaction with another molecule is prevented or retarded in rate. A sterically hindered compound may be further defined as a compound having substitutents whose physical bulk does not require confinement within volumes insufficient for the exercise of their normal behavior as discussed in "Organic Chemistry," D. J. Cram and G. Hammond, $2^{nd}$ edition, McGraw-Hill Book Company, N.Y., page 215 (1964).

It is known that displacement of the third halo group in reactions with sterically hindered aliphatic or aromatic hydroxyl-containing compounds is quite difficult. The substitution rate of the reaction depends in part by the steric bulk of the hydroxyl-containing compounds.

Applicants have found that in the two-stage process of the present invention, after a conversion rate of 95% or more is achieved, the use of certain acid acceptors economically and surprisingly drive a reaction, in which one of the reactants is sterically hindered, to at least 98% completion to produce acid esters.

I. Reaction to produce Acid Esters. In one embodiment, acid esters are organic phosphites produced by reacting an acid halide such as a phosphorous halide with aliphatic or aromatic hydroxyl-containing compounds, wherein the halides are displaced by the hydroxyl-containing compounds.

Examples of organic phosphites include di-substituted phosphites or chlorophosphites. In one embodiment, the acid esters are diphosphites based upon pentaerythritol, wherein the phosphite esters are prepared from the reaction of an chlorophosphite obtained by reaction of phosphorous trihalide with pentaerythritol and further reaction with a hydroxyl-containing compound. The diphosphites containing alkyl, aryl, or alkyl-substituted aryl groups are especially desirable compounds due to their enhanced hydrolytic stability, ease of handling and compatibility with a wide variety of polymeric systems.

In another embodiment, the acid esters are organic phosphite esters having the formula $P-(OR)_3$.

In another embodiment, the acid esters are phosphonites of the formula $(RO)_2P-R$, wherein each R is independently selected from alkyl, aryl, alkaryl, aralkyl and substituted alkyl, aryl, alkaaryl and arakyl groups. Examples of organic phosphites include triphenyl phosphite, tris(2,5-di-tert-butylphenyl)phosphite, tris(2-tert-butylphenyl)phosphite, tris(2-phenylphenyl)phosphite, tris(2-(1,1-dimethylpropyl)phenyl)phosphite, tris(2-cyclohexylphenyl)phosphite, tris(2-tert-butyl4-phenylphenyl)phosphite, tris(2-tert-butyl-4-methylphenyi)phosphite, tris(2,4-di-tert-amylphenyl)phosphite, tris(2,4-di-tertbutylphenyl)phosphite and (2,4,6-tri-tert-butylphenyl)-2-butyl-2-ethyl-1,3-propanediol-phosphite.

In yet another embodiment, the acid esters are carboxylic acid esters. In one embodiment, the carboxylic acid esters are aromatic represented carboxylic acid esters by the general formula ARC(O)OH having between $C_8$ to $C_{40}$ total and produced by reacting a corresponding acyl halide with hydroxyl-containing compounds, wherein the halides are displaced by the hydroxyl-containing compounds. Examples of carboxylic acid esters include benzoates, toluates, anisates and the like.

Reactants—Acid Halides. In one embodiment, the acide halides are phosphorous halides $PX_3$, the phosphorous halide compounds include chlorine, fluorine, bromine, iodine and mixtures thereof. Examples include phosphorous trichloride or phosphorous tribromide.

In one embodiment, the acid halides are di-substituted phosphites. For example, di-substituted phosphorohalidites of the general formula: wherein each of R1 and R2 are independently a $C_{1-20}$ alkyl, aryl, or alkaryl moiety and Y is a halogen.

In another embodiment, R1 and R2 are interconnected (i.e., the

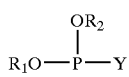

residual of a diol) such that the di-substituted phosphite is a cyclic phosphite.

In yet one embodiment, the acid halides are phosphites based on butyl ethyl propanediol, e.g., 2-butyl-2-ethyl-1,3-propanediol-monochlorophosphite.

In another embodiment, the acid halides are acyl halides, which include the corresponding halides of the carboxylic acid esters, i.e., substituents derived from the corresponding carboxylic acid group by removing the OH of the carboxyl group thereby providing a free valence. Examples are acyl halides selected from the group of of benzoyl chloride, benzoyl bromide, trichloroacetyl chloride, p-chlorobenzoyl chloride, p-methoxybenzoyl chloride, and methyl benzoyl chloride.

Reactants—Sterically Hindered Alcohol or Phenol Reactant. In one embodiment of the invention, the hydroxyl-containing compounds in the present invention are sterically hindered phenols of the general formula:

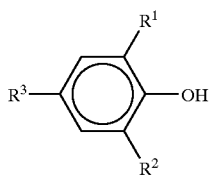

4 wherein each $R^1$, $R^2$, and $R^3$ is independently selected from the group consisting of hydrogen, methyl, ethyl, n-propyl, iso-propyl, n-butyl, t-butyl, t-amyl, t-hexyl, cyclohexyl, t-pentyl, t-octyl, and cumyl.

3. Acid acceptor for increasing the conversion rate. The acid acceptor of the present invention functions to facilitate the substitution of the last halide moiety in the acid halides by the hydroxyl-containing compound and drive the reaction toward completion.

In the first stage of the process of the invention, an acid acceptor selected from acid acceptors or dehydrohalogenation agents commonly used in the prior art is used to achieve about 95% conversion. Examples include amines, pyridines, pyrrolidines, amides, an aqueous alkalide material, or a hydroxide of alkaline metal or alkaline earth metal. Examples of the alkaline acceptors include sodium carbonate, potassium carbonate and hydroxides of the alkaline metal or alkaline earth metal such as sodium hydroxide, calcium hydroxide and the like.

The arnines may be primary amine, secondary amine, and tertiary amine commonly used in the art. The amine may be any amine which scavenges hydrogen chloride and/or hydrogen bromide as the case may be. The amine may be aliphatic, cyclic or aromatic. A single amine or a mixture of amines may be used as desired. The cyclic amines usually contain at least about 5 carbon atoms, preferably from 5 to about 10 carbon atoms. Examples include N-methylpyrrolidine, N-methylpiperidine, and N-phenylmorpholine, and 1,8-diazabicyclo[5,4,0]undec-7-one. The aromatic amines frequently contain at lest 5 carbon atoms with 5 to 15 being preferred. Examples include N,N-dimethylanilines, N,N-dimethylxylidines, pyridine, and alkyl derivative of pyridine. These may include polymer supported amines.

In one embodiment, the amine employed contains at least 3 carbon atoms. Usually the amine contains from 3 to about 18 carbon atoms. Examples include trialkyl amines such as tripropyl amine, tributyl amine, and triheptyl amine. Examples of the pyridines include pyridine, piconline and the like. In one embodiment, 1-methyl-2-pyrrolidine is used.

In another embodiment, an amide is used. Examples of the amides include N,N-dimethylformamide, N,N-dimethylacetylamide and the like.

In the second stage of the process of the invention, after a 95% conversion rate is achieved, a second acid acceptor is used to bring the conversion rate to at least about 98%.

The acid acceptor for used in the second stage of the process is selected from the group of cyclic amines consisting of 1,5-diazabicyclo[4.3.0]non-5-ene (DBN), 1,8-diazabicyclo[5.4.0]undec-7-ene (DBU), 4-(dimethylamino) pyridine (DMAP), 1,4-diazabicyclo[2.2.2]octane (DABCO), and mixtures thereof. In one embodiment, DBU is used.

In the practice of the present invention employing a two-stage process, the cyclic amine acid acceptor leads to conversion degrees of at least about 98%, and in one embodiment, of at least 99% in terms of the displacement of the halide group by the sterically hindered alcohol or phenol.

The acid acceptor is used in at least about an equimolar amount based on their nitrogen content relative to the molar amount of halide present in the reaction.

In embodiments wherein the acid halide is a phosphorous halide, it is considered that an intermediate halogenophosphite, i.e., di-substituted phosphorohalidite, is produced. In the displacement of the third halide moiety from the intermediate halogenophosphite (or the halide moiety from the reactant di-substituted phosphorohalidite, e.g., 2-butyl-2-ethyl-1,3-propanediol-monochlorophosphite), the degree of conversion to the desired phosphoric acid ester is adversely affected by steric considerations of both the intermediate halogenophosphite and the hydroxyl-containing compound. To drive the conversion rate to at least 99% plus, the acid acceptor is used in an amount such that the molar ratio of nitrogen in the acid acceptor to the phosphorohalidite is at least about 1:1. In one embodiment of the invention, this molar ratio is about 1:1 to 1.

4. Other components. In one embodiment of the invention, an organic solvent is used. The organic solvent may be any solvent that does not inhibit the reaction, and is not specifically limited. Examples thereof include aromatic hydrocarbon, aliphatic hydrocarbon, oxygen-containing hydrocarbon, halogenated hydrocarbon and the like. Examples of solvents include benzene, toluene, xylene, heptane, dichloromethane and the like.

II. Process to Prepare Acid Esters. The process according to the present invention is performed in devices known to be suitable for the purpose.

In the first stage, the sterically hindered hydroxyl-containing compound is placed optionally together with a solvent into a reaction vessel. An acid halide, i.e., the acyl halide, phosphorous trihalide, or the di-substituted phosphite, is then added. After the addition of at least an acid acceptor selected from primary amine, secondary amine, and tertiary amine acid acceptors, the reaction mixture is stirred until the reaction goes to equilibrium with a conversion rate at least 90% completion and preferably about 95% completion. Stirring is preferably carried out with heating of up to about 200° C. in order to accelerate the reaction. The pressure of the reaction system is maintained between about 50 millimeters mercury absolute to atmospheric pressure.

Any optional amine salt, e.g. tripropylamine hydrochloride, added in the first stage is optionally removed by filtration before the second stage. In the second stage, the cyclic amine acid acceptor of the present invention is added to the reaction mixture. The reaction mixture continues to be stirred until the reaction is complete with a conversion rate of at least about 98% to yield the desired tri-substituted acid ester.

After obtaining the desired conversion rate, any optional solvent used in the reaction may be removed by flash distillation or another solvent removal technique or alternatively, the desired end-product acid ester can be isolated by using known methods, by precipitation or crystallization, optionally after the removal of the optional inert solvent. The hydrogen halide salts formed may be collected via filtration and washed with another solvent for later recovery and a vacuum can be used to effect complete separation.

In an embodiment wherein the acid halide is a phosphorous halide and an intermediate di-substituted phosphorohalidite is generated, the reaction of the hydroxy-substituted compound with the intermediate di-substituted phosphorohalidite in the presence of the cyclic amine acid acceptors may be conducted in the same reaction vessel that was employed to produce the di-substituted phosphorohalidite.

III. Recovery and Recycling of Cyclic Amine Acid Acceptor. In one embodiment of the invention and in the next last stage of the process, the acid acceptor of the present invention is isolated and recovered.

In facilitating the reaction to yield the desired tri-substituted acid ester and driving the reaction to at least 98% completion, the cyclic amine acid acceptor forms an amine hydrogen halide. The cyclic amine acid acceptor can be efficiently recovered in a waterless step to minimize the formation of mono-amino compounds and maximize recovery yields.

In this recovery stage, an alcoholate compound selected from the group of an alkali metal alcoholate and a quaternary ammonium alcoholate is added to the mixture of an anhydrous solvent and the amine hydrogen halide salts, and the reaction is allowed to go to equilibrium. The reaction mixture is filtered to remove any unreacted amine hydrogen halide salts for further recovery. The filtrate is then distilled to remove the anhydrous solvent and the recovered acid acceptor of the present invention.

Examples of anhydrous solvents wherein the cyclic amine salts dissolves include aromatic hydrocarbon, aliphatic hydrocarbon, oxygen-containing hydrocarbon, halogenated hydrocarbon and the like. In one embodiment, methanol is used.

Examples of alkali metal alcoholates include lithium methylate, sodium methylate, potassium methylate, lithium ethylate, sodium ethylate, potassium ethylate, sodium isopropylate, etc.; and a quaternary ammonium alcoholate such as tetramethylammonium methylate, tetraethylammonium methylate, tetramethylammonium ethylate, etc. Mixtures of alcoholates may be used. In one embodiment, sodium methylate is used.

EXAMPLES

The process of the invention is illustrated by the following examples, which are not, however, to be construed as limiting in anyway.

Example 1

A reaction vessel was charged with 91.35 grams(0.57 moles) 2-butyl-2-ethyl-1,3-propanediol. The reaction vessel was cooled using a wet ice bath. 78.28 grams (0.57 moles)of phosphorus trichloride was added over a period of 3 hours with the generated hydrogen chloride gas being collected by passing through a scrubber containing water. The mixture was allowed to stir overnight slowly warming to room temperature. The reaction resulted in 128.06 grams (0.57 moles) of the 2-butyl-2-ethyl-1,3-propanediol monochlorophosphite (99.46% title compound by gas chromatography). This reaction product can also be prepared in the presence of an optional solvent as previously described.

An amount equivalent to 22.47 grams (0.10 moles) of the monochlorophosphite was added to a reaction vessel containing a mixture of 34.78 grams (~0.13 moles) 2,4,6-tri-t-butylphenol and 27.44 grams (~0.193 moles) of tripropylamine at 60° C. The reaction mixture was heated to about 120° C. with stirring for a period of three hours. The mixture was cooled to ~26° C. and pressure filtered through a filtering funnel. About 0.80 grams of acid acceptor 1,8-diazabicyclo[5.4.0]undec-7-ene (DBU) was added to the filtrate and the mixture was heated to 120° C. for a period of 1 hour. Gas chromatographic analysis of the filtrate both before and after treatment with DBU gave the following results.

|  | Before treatment | After treatment |
|---|---|---|
| Residual BEPD chlorophosphite | 1.055% | None Detected |
| Residual 2,4,6-Tri-t-butylphenol | 9.64% | 8.14% |
| Product | 48.52% | 51.45% |
| Tripropylamine | 39.75% | 39.77% |

The product in solution, after isolation, provided a conversion of about 99% plus after treatment, versus about less than 97% before treatment with the acid acceptor of the present invention.

Example 2

In an example, the DBU:HCL salts collected from various exaples including Example 1 were washed with tripropylamine, pressure filtered and then dissolved in methanol. Sodium methylate was slowly added at 25% the weight of the washed DBU:HCL salts dissolved in methanol. Cooling water was supplied to the filter/reactor jacket before the sodium methylate addition started. The mixture was agitated for a period of 1 hour after the addition was complete. The stirring was stopped and the solids were allowed to settle for a period of thirty minutes. The mixture was pressed from the filter/reactor through a 20 micron (maximum) filter screen. The filter cake was washed with 25 grams of methanol and pressed out using nitrogen, without agitation. A second filter cake wash was performed using 10 grams of methanol. After filtration was complete, the kettle was heated to 80° C. while purging the cake with nitrogen.

The combined filtrates were transferred to a distillation kettle. The methanol was removed by heating under nitrogen at atmospheric pressure to approximately 100° C. and recycled into the next batch of salts to be recovered. The distillation kettle was next cooled to 70° C. and vacuum was applied. Any tripropylamine present was removed at reduced pressure. After the majority of the tripropylamine was removed, the distilled DBU is collected. Gas chromatography indicates that the distillate is at least about 97% DBU, giving a DBU yield of at least 85%.

Having described the invention, that which is claimed is:

1. A process for preparing sterically hindered acid esters comprising:
   a. reacting a sterically hindered phenol with an acid halide in the presence of an acid acceptor for a conversion rate of at least 90%, said acid accepter is selected from primary amine, secondary amine, and tertiary amine;
   b. further reacting said sterically hindered phenol with said acid halide in the presence of a cyclic amine acid acceptor selected from the group consisting of: 1,5-diazabicyclo[4.3.0]non-5-ene (DBN), 1,8-diazabicyclo[5.4.0]undec-7-ene (DBU), 4-(dimethylamino)pyridine (DMAP), 1,4-diazabicyclo[2.2.2]octane (DABCO), and mixtures thereof, wherein said cyclic amine acid acceptor is present in an amount sufficient to drive said reaction to at least 98% completion.

2. The process of claim 1, wherein the acid acceptor selected from the tertiary amine group consisting of: trialkylamine, N,N-dimethylaniline, N,N-diethylaniline, Hunig base, N,N-dimethyl-aniline, and mixtures thereof.

3. The process of claim 1, wherein the cyclic amine acid acceptor is 1,8-diazabicyclo[5.4.0]undec-7-ene (DBU).

4. The process of claim 1, wherein said sterically hindered phenol is

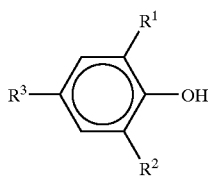

of the general formula:
   wherein each R¹, R², and R³ is independently selected from the group consisting of hydrogen, methyl, ethyl, n-propyl, iso-propyl, n-butyl, t-butyl, t-amyl, t-hexyl, cyclohexyl, t-pentyl, t-octyl, and cumyl.

5. The process of claim 1, wherein said acid halide is a phosphorous trihalide and said acid esters are organic phosphite esters having the formula (I):

wherein each R is independently selected from alkyl, aryl, alkaryl, aralkyl and substituted alkyl, aryl, alkaryl and arakyl groups.

6. The process of claim 1, wherein said acid halide is a phosphorous trihalide and said acid esters are di-substituted cyclic phosphites of the general formula:

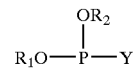

wherein each of R1 and R2 are independently a $C_{1-20}$ alkyl, aryl, or alkaryl moiety and Y is a halogen and wherein R1 and R2 are interconnected.

7. The process of claim 6, wherein the acid esters are di-substituted chlorophosphites.

8. The process of claim 6, wherein the acid esters are di-substituted cyclic phosphites based upon butyl ethyl propanediol.

9. The process of claim 1, wherein said cyclic amine acid acceptor is added to the reaction mixture in an amount of at least about an equimolar amount based on nitrogen content in said acid acceptor relative to the molar amount of halide present in the reaction mixture.

10. The process of claim 9, wherein the molar ratio of nitrogen in the cyclic amine acid acceptor to the amount of halide present in the reaction mixture is at least about 1.1:1.

11. The process of claim 10, wherein the reaction for forming the sterically hindered acid esters is at least 99 plus % completion and the unreacted cyclic amine acid acceptor forms an amine hydrogen halide salt.

12. The process of claim 11, further comprising dissolving the amine hydrogen halide salt in a non-reactive anhydrous solvent and reacting said amine hydrogen halide salt dissolved in an anhydrous solvent with an alcoholate compound.

13. The process of claim 12, wherein said alcoholate compound is selected from the group consisting of: lithium methylate, sodium methylate, potassium methylate, lithium ethylate, sodium ethylate, potassium ethylate, sodium isopropylate, quaternary ammonium alcoholate, and mixtures thereof.

14. The process of claim 12, wherein said an anhydrous and non-reactive solvent is selected from the group consisting of: aromatic hydrocarbons, aliphatic hydrocarbons, oxygen-containing hydrocarbons, halogenated hydrocarbons, and mixtures thereof.

15. The process of claim 12, wherein said an anhydrous solvent is methanol and said alcoholate compound is sodium methylate.

* * * * *